United States Patent [19]
Oppawsky et al.

[11] Patent Number: 6,062,857
[45] Date of Patent: May 16, 2000

[54] MANUALLY OPERATED EJECTOR DEVICE

[75] Inventors: Steffen Oppawsky, Bad Homburg; Dieter Schödel, Wiesbaden, both of Germany

[73] Assignee: Heracus Kulzer GmbH & Co. KG, Hanau, Germany

[21] Appl. No.: 09/266,642

[22] Filed: Mar. 11, 1999

[30] Foreign Application Priority Data

Mar. 13, 1998 [DE] Germany .......................... 198 10 950

[51] Int. Cl.$^7$ .................................................. A61C 5/04
[52] U.S. Cl. ................. 433/89; 433/90; 222/137
[58] Field of Search ................................ 433/89, 90, 80; 222/137, 145.6, 327, 459; 604/135

[56] References Cited

U.S. PATENT DOCUMENTS

| | | | |
|---|---|---|---|
| 4,295,828 | 10/1981 | Rudler ....................................... | 433/90 |
| 4,382,789 | 5/1983 | Colombo et al. .......................... | 433/89 |
| 4,472,141 | 9/1984 | Dragan ...................................... | 433/90 |
| 5,125,836 | 6/1992 | Dragan et al. ............................. | 433/90 |
| 5,306,147 | 4/1994 | Dragan et al. ............................. | 433/90 |
| 5,489,207 | 2/1996 | Dragan et al. ............................. | 433/90 |
| 5,743,436 | 4/1998 | Wilcox et al. ............................. | 433/90 |

*Primary Examiner*—Gene Mancene
*Assistant Examiner*—Pedro Philogene
*Attorney, Agent, or Firm*—Norris, McLaughlin & Marcus, P.A.

[57] ABSTRACT

A manually operated ejector device for containing a cartridge loaded with viscous material, having a chamber with a front end adapted to contain the cartridge and a back end, a piston disposed in the chamber for engagement in the cartridge, a handle arranged at the back end of the chamber, and a lever displaceable relative to the chamber and the handle for driving the piston in order to drive the latter in its longitudinal direction toward the front end of the chamber. To improve the safety of the handling of the ejector device, the piston has a spring case and a plunger, the spring case having a chamber whose one end is closed and whose other, front end has an opening, the transition between the chamber and the opening being limited by an abutment surface facing the chamber. The plunger furthermore has a cylinder guided through the opening and, on its back end within the chamber, a plunger head which has a greater diameter than the opening, at least in a direction across the longitudinal axis of plunger and spring case. Between the back end of the plunger head facing away from the cylinder there is disposed a spring unit which is compressible in its longitudinal direction parallel to the longitudinal direction of the piston, the travel stroke of the spring unit being at least as great as the distance to which the spring housing is displaceable in the guide sleeve.

10 Claims, 3 Drawing Sheets

MANUALLY OPERATED EJECTOR DEVICE

BACKGROUND OF THE INVENTION

The invention relates to a manually operated ejector device for containing a cartridge loaded with viscous material, having a chamber with a front end adapted to contain the cartridge and a back end, a piston disposed in the chamber for engagement in the cartridge, a handle arranged at the back end of the chamber, and a lever displaceable relative to the chamber and the handle for driving the piston in order to drive the latter in its longitudinal direction toward the front end of the chamber.

Such ejector devices are disclosed, for example, in U.S. Pat. No. 5,489,207 or in U.S. Pat. No. 4,472,141. The cartridge placed in the front end of the chamber contains a viscous dental material, for example for filling dental cavities, which is ejected by means of the piston of the ejector device and forced into a dental cavity. For this purpose the piston attacks the back end of the stopper disposed in the cartridge and closes same, which upon the forward movement of the piston is also forced forward and at the same time ejects the viscous material from the outlet tip at the forward end of the cartridge. The travel stroke of the piston is limited by the limited length of displacement of the stopper of the cartridge. In cases in which the cartridge is not optimally adapted to the ejector device and the length of displacement of the piston of the ejector device, or in cases in which the material in the cartridge has too great a viscosity or is more or less completely hardened, as can occur with polymerizing dental materials if the cartridge is not stored properly, the danger exists that, if the pressure exerted by the dentist on the plug of the cartridge is too great, the cartridge may be destroyed in the extreme case. In the event of such destruction, parts of the cartridge may be accelerated under high pressure into the patient's jaw and there lead to considerable injury.

SUMMARY OF THE INVENTION

The invention is addressed to the problem of at least partially remedying the disadvantages of the known state of the art and improving safety in the operation of the ejector device.

The problem is solved in an ejector device of this kind in that the piston has a spring housing and a ram, and the spring housing has a chamber whose one end is closed and whose other, front end has an opening, the transition between the chamber and the opening being limited by an abutment surface facing the chamber, in that the ram has a cylinder guided through the opening and has at its back end within the chamber a ram head which at least in one direction across the longitudinal axis of ram and spring housing has a greater diameter than the opening, and in that between the back end of the ram head remote from the cylinder and the closed end of the chamber a spring unit compressible in its length parallel to the longitudinal direction of the piston is disposed, the stroke of the spring unit being at least as great as the distance to which the spring housing can be displaced in the chamber.

The spring constant must be selected such that, in the state of the viscous material that is normal for its use, it is not compressed or is compressed but slightly. The permissible maximum force which may act upon the plug of the cartridge or upon the lever system in order to prevent destruction of the cartridge or ejector device, can easily be learned for the particular application. The spring unit should have a bias. For example, in the case of ejector devices for dental cartridges containing dental filling material, this bias should be approximately 400–500 N, preferably about 430 N. By such an arrangement the assurance is given that in cases in which, for example, the piston is too long for a cartridge not best fitted to the ejector device, or in those in which the material in the cartridge has cured, the tip of the cartridge will be torn off by excessive pressure on the piston, or the lever of the ejector device will be destroyed. For when the bias is overcome the spring is compressed. In the case of the preferred use of a helical plate spring or a plate spring, which can be made especially of tightening disks, this compression takes place continually. The lever, which in the foremost possible position of the piston cannot at first be moved any further, can be moved again by a limited amount, namely the spring travel stroke, when the bias force is overcome, because after overcoming the bias force upon the compression of the spring it urges the spring case forward without moving the plunger. This change can be perceived by the dentist, since he is able to move the lever without forcing material out of the cartridge as long as he is given a signal to halt any further pressure on the lever of the ejector device. Since the travel stroke is equal to or greater than the distance over which the spring case can be moved by the lever until the lever reaches its abutment position, destruction of the cartridge by the plunger is impossible. The spring unit can best have a spring travel stroke of about 8 to 15 mm, preferably about 10 to 12 mm, depending on the length of the inserted cartridge.

It is desirable for a guide rod to be disposed in axial symmetry with the axis of the plunger at the end of the plunger remote from the cylinder, the spring unit being guided on its circumference. Furthermore, it is advantageous to provide an axially symmetrical bore at the rear, closed end of the spring case, and to give it a diameter greater than the diameter of the guide rod and a length at least as great as the travel stroke of the spring unit, so that the guide rod will enter this bore when the spring is compressed and the spring case will not be hampered in its movement relative to the plunger. Furthermore, it is advantageous, for assembly purposes for example, that a roll pin be provided in the closed end of the spring case, perpendicular to the length of the spring housing.

An embodiment of the invention will be explained below with the aid of a drawing, wherein:

DETAILED DESCRIPTION OF THE INVENTION

Figure 1:
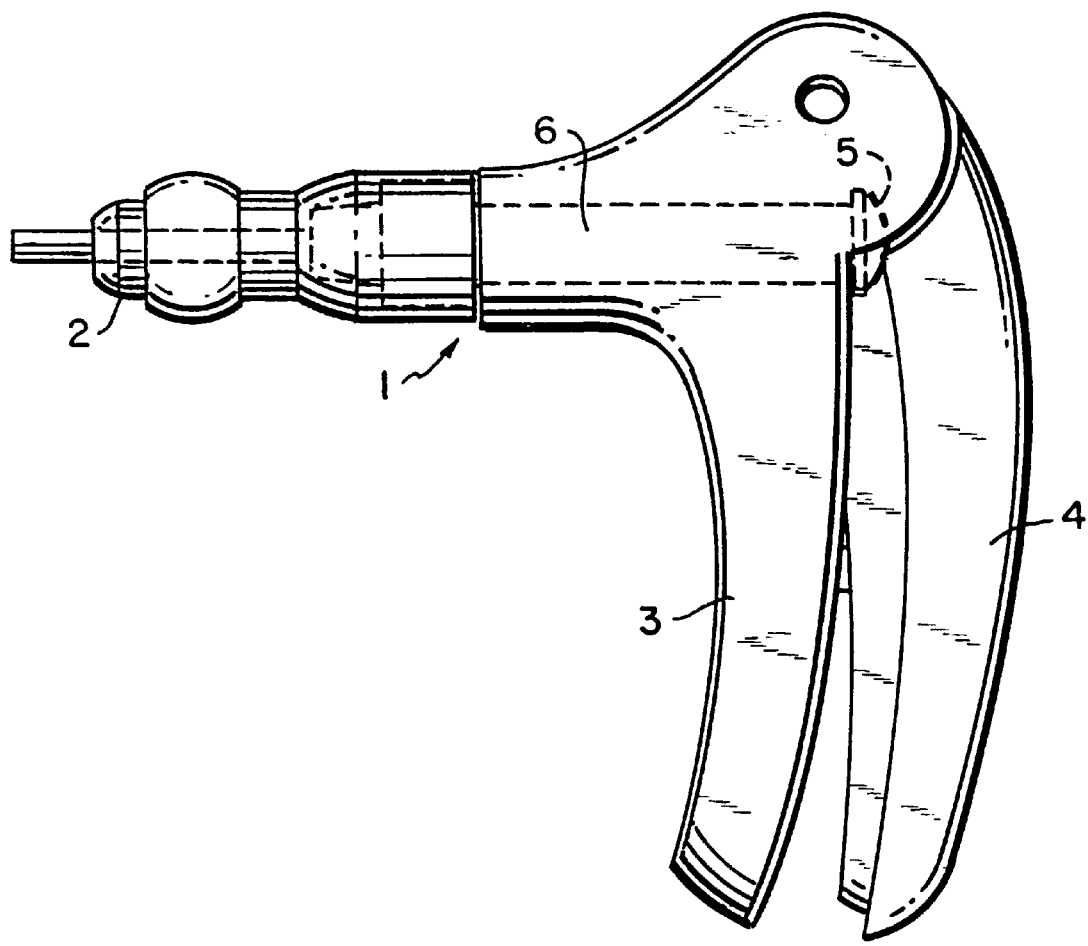
FIG. 1 is a schematic representation of an ejector device according to the invention.

In FIG. 1 is shown an ejector device which is designed to receive cartridges containing dental material and to be used by the dentist. The ejector device has a guiding sleeve 1 at whose front end is a mounting 2 for a cartridge, and at whose back end a handle 3 is disposed. On the handle 3 there is disposed a lever 4 which can be moved relative to the guiding sleeve and to the handle 3, and which presses against the back end 5 of a piston 6. By this pressure the piston 6 is driven forward into the cartridge so that the dental material is forced out of the cartridge and into a tooth cavity, for example. The piston 6 is so designed that, even when very great pressure is applied to the lever 4 by the dentist, neither the cartridge nor the ejector device itself can be destroyed.

Figure 2:
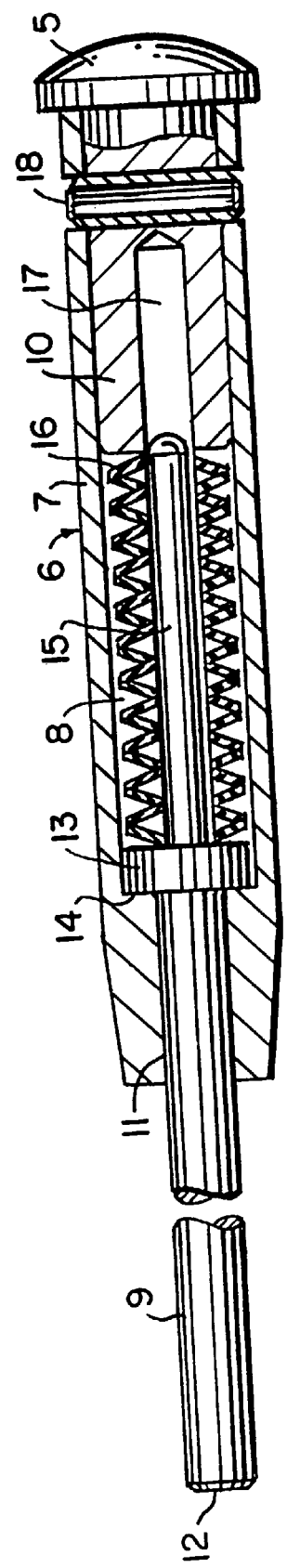
FIG. 2 is a cross section through the piston of the ejector device.

The construction of the piston 6 is shown in FIG. 2. The piston 6 has a spring case 7 with a chamber 8 as well as a plunger 9. The chamber 8 of the spring case 7 is closed at its back end 10 and has at its front end an opening 11 through which the barrel of the plunger 9 passes. The plunger terminates at its front end in an abutment 12 for engagement in the cartridge and has at its back end, inside of the chamber 8, a plunger head 13 of a diameter larger than the diameter of the opening 11, so that the head 13 of the plunger 9, in its foremost position, will come into contact with an abutment surface 14 forming the transition between the chamber 8 and the opening 11. At the back end of the plunger head 13 remote from the opening 11, a guide rod 15 is disposed in axial symmetry with the axis of the plunger 9 and serve to guide the spring unit 16 disposed in the chamber 8. The spring unit 16 is a plate spring. It is given a bias of about 430 N and has a travel stroke of about 11 mm. At the rear end 10 of the chamber 8 of the spring case 7, remote from the barrel of the plunger 9, there is an axially symmetrical bore 17 whose diameter is greater than the diameter of the guide rod 15 and whose length is at least as great as the travel stroke of the spring unit 16. At the back end 10 of the spring case 7, just ahead of the rounded back end 5, there is a roll pin 18 which facilitates the assembly of the piston 6.

Figure 3:
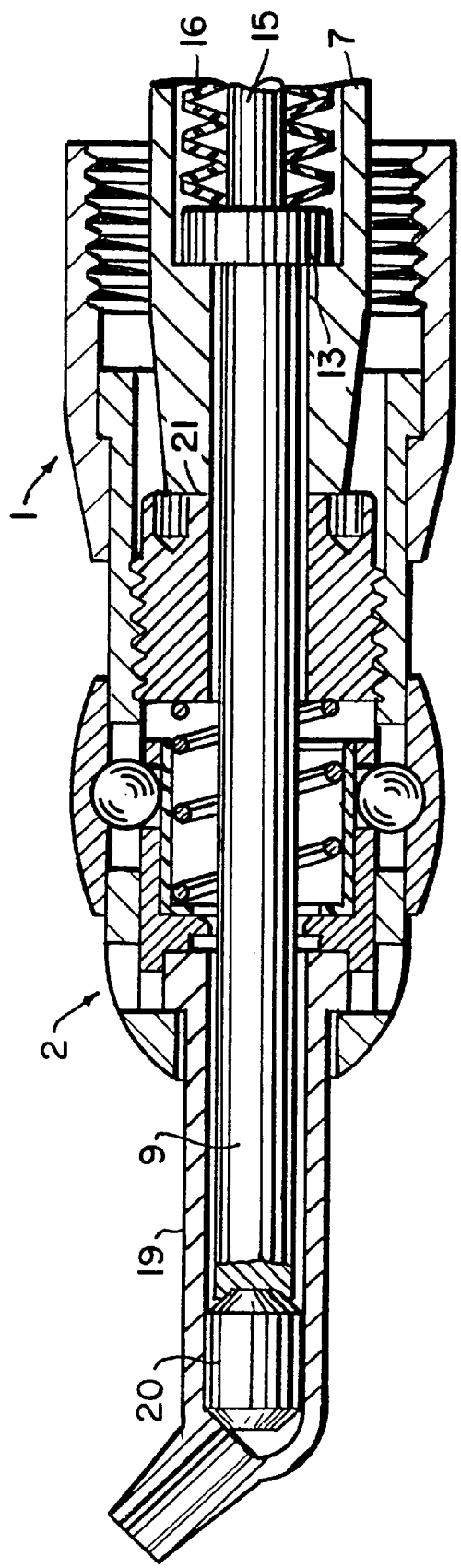
FIG. 3 is a cross section through the front part of the ejector device with a plunger entering the cartridge.

FIG. 3 shows the front end of the ejector device with the inserted cartridge 19, the plunger 9 of the piston being in its forward position. The plug 20 disposed in the cartridge has in this case forced the dental material contained in the cartridge 19 nearly all the way out of the latter. If the ejector device and cartridge 19 are properly matched, the plunger 9 is here in its extreme forward position. The spring case 7 of the piston 6 is likewise in its forward position and is in contact with a limiting abutment 21 within the guide sleeve 1.

What is claimed is:

1. A manually operated ejector device for a cartridge which is charged with viscous material, comprising: a guide sleeve with a front end adapted to receive a cartridge and a rear end, a piston which is longitudinally displaceable in the guide sleeve for engaging the cartridge, a handle disposed at the rear end of the guide sleeve and a lever which is movable relative to the guide sleeve, wherein the handle engages the piston to longitudinally displace it toward the front end of the guide sleeve, wherein the piston has a spring case and a plunger, the spring case has a chamber with one closed end and another forward end having an opening, a transition between the chamber and the forward end opening including an abutment surface facing the chamber, wherein the plunger has a cylinder guided through the forward end opening and a plunger head at its rear end within the chamber, said plunger head having a larger diameter than the opening, and between the rear end of the plunger head remote from the cylinder and the closed end of the chamber a spring unit compressible in its length parallel to the longitudinal direction of the piston is disposed, the spring travel stroke of the spring unit being at least as great as the distance to which the spring chamber is displaceable in the guide sleeve.

2. The manually operated ejector device according to claim 1, wherein the spring unit is configured as a plate spring or as a helical plate spring.

3. The manually operated ejector device according to claim 2, wherein the plate spring is formed by tightening disks.

4. The manually operated ejector device according to claim 1, wherein at the rear end of the plunger remote from the cylinder a guide rod is disposed in axial symmetry with the axis of the plunger and that the spring unit is guided on the circumference of the guide rod.

5. The manually operated ejector device according to claim 4, wherein in the rear closed end of the spring case an axially symmetrical bore is disposed, whose diameter is greater than the diameter of the guide rod and its length is at least as great as the spring travel stroke of the spring unit.

6. The manually operated ejector device according to claim 1, wherein the spring unit has a travel stroke of about 8 to 15 mm.

7. The manually operated ejector device according to claim 6, characterized in that the spring unit has a travel stroke of about 10 to 12 mm.

8. The manually operated ejector device according to claim 1, wherein the spring unit is biased.

9. The manually operated ejector device according to claim 8, wherein the spring unit has a bias of about 400–500 N.

10. The manually operated ejector device according to claim 1, further comprising a roll pin perpendicular to the length of the spring case and disposed in the closed end of the spring case.

* * * * *

UNITED STATES PATENT AND TRADEMARK OFFICE
CERTIFICATE OF CORRECTION

PATENT NO.    : 6,062,857
DATED         : May 16, 2000
INVENTOR(S)   : Oppawsky et al.

It is certified that error appears in the above-identified patent and that said Letters Patent is hereby corrected as shown below:

<u>Title page,</u>
Title of Assignee, delete "Heracus" and substitute -- Heraeus --

Signed and Sealed this

Sixteenth Day of April, 2002

*Attest:*

JAMES E. ROGAN
*Attesting Officer*     *Director of the United States Patent and Trademark Office*

UNITED STATES PATENT AND TRADEMARK OFFICE
CERTIFICATE OF CORRECTION

PATENT NO.   : 6,062,857
DATED        : May 16, 2000
INVENTOR(S)  : Oppawsky et al.

It is certified that error appears in the above-identified patent and that said Letters Patent is hereby corrected as shown below:

<u>Title page,</u>
Item [73], Assignee, change "Heracus" to -- Heraeus --

Signed and Sealed this

Twenty-first Day of January, 2003

JAMES E. ROGAN
*Director of the United States Patent and Trademark Office*